United States Patent [19]

Szakasits et al.

[11] Patent Number: 4,534,207
[45] Date of Patent: Aug. 13, 1985

[54] REFORMER PROCESS ANALYZER

[75] Inventors: Julius J. Szakasits; Robert E. Robinson, both of Houston, Tex.

[73] Assignee: Shell Oil Company, Houston, Tex.

[21] Appl. No.: 691,727

[22] Filed: Jan. 15, 1985

Related U.S. Application Data

[63] Continuation of Ser. No. 499,122, May 31, 1983, abandoned.

[51] Int. Cl.³ ............................................. G01N 31/08
[52] U.S. Cl. .................................................... 73/23.1
[58] Field of Search ........................ 73/23.1; 436/161; 422/89; 55/67, 197, 386

[56] References Cited

U.S. PATENT DOCUMENTS 3,550,428 12/1970 Mator et al. ......................... 73/23.1
3,865,562 2/1975 Ayers et al. ............................ 55/67

FOREIGN PATENT DOCUMENTS 1123718 8/1968 United Kingdom ................. 73/23.1

OTHER PUBLICATIONS

R. D. McCoy et al., "On-Line Computer Controlled Chromatograph for the Analysis of Catalytic Reformer Streams," Texas A and M Instrumentation Symposium, pp. 20-26, Jan. 1970.
H. Boer et al., "An Automatic PNA Analyzer for (Heavy) Naphtha," *Chromatographia* 4, pp. 300-308, 1971.
H. Boer et al., "Better Gasoline Chromatography," *Hydrocarbon Processing*, pp. 80-84, Feb. 1972.
H. Boer et al., "An Automatic PNA Analyzer for Under 200° C. Fraction Contained in Higher Boiling Product," *Chromatographia*, vol. 13, No. 8, pp. 500-512, Aug. 1980.

*Primary Examiner*—Stephen A. Kreitman

[57] ABSTRACT

An apparatus for analyzing a hydrocarbon sample comprising paraffins, naphthenes and aromatics. The subject apparatus comprises means for providing a sample, a polar column, a 13X molecular sieve coated open tubular column, a nonpolar stationary phase column, a valve means, detection means and means for supplying gas.

30 Claims, 6 Drawing Figures

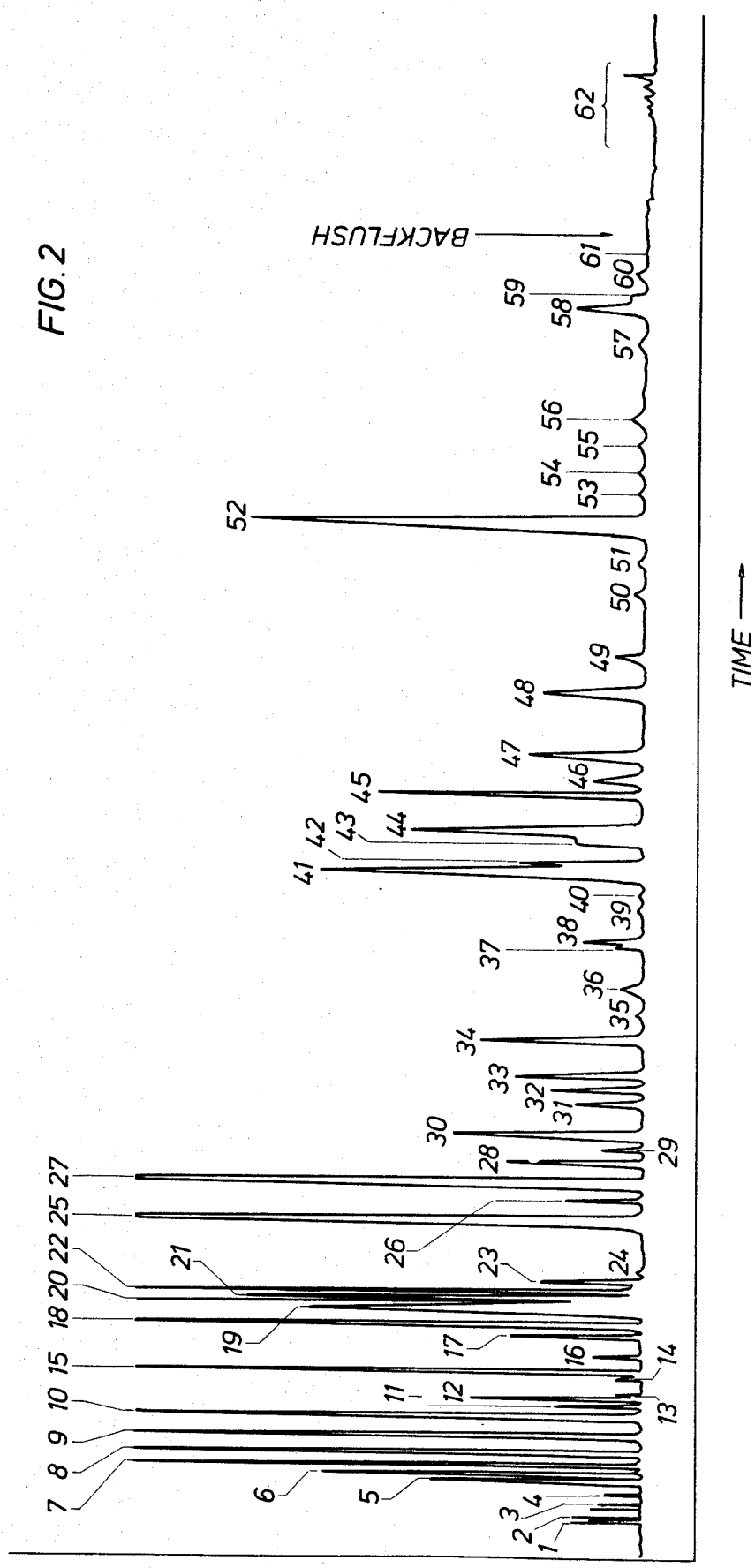

REFORMER PROCESS ANALYZER

This is a continuation of application Ser. No. 499,122, filed May 31, 1983, now abandoned.

BACKGROUND OF THE INVENTION

This invention relates generally to gas chromatography and, more particularly, to the paraffin, naphthene and aromatic analysis of reformer feedstock and product.

Frequent changes in feedstock quality for catalytic reformers has created a need for an on site instrument which can quickly provide information on feed and product composition changes to assist in plant surveillance and process tuning. The failure to recognize poor plant performance or upset at an early stage can lead to a serious loss in reformer yields and/or a premature need for catalyst regeneration. In the past characterizing of reformer feeds and products has generally been done by a combination of gas chromatography and analytical chemistry methods in a central laboratory which is usually remote from the refinery. This technique is time consuming and often leads to a sizable delay between the times the sample is taken and the results are made available to the refinery.

Therefore, it is an object of the present invention to provide a method of and apparatus for analyzing a hydrocarbon sample from a reformer process to provide a rapid and detailed analysis of the paraffin, naphthene and aromatic composition of the sample.

SUMMARY OF THE INVENTION

In accordance with the present invention there is provided an apparatus for analyzing a hydrocarbon sample comprising paraffins, naphthenes and aromatics. The subject apparatus comprises means for providing a sample, a polar column, a 13X molecular sieve coated open tubular column (13X MSCOT column), a mixed binary phase column, a nonpolar stationary phase column, a valve means, detection means, temperature controlling means and means for supplying gas. A first means for supplying gas and the valve means are connected to the sample providing means. The polar column is connected to the valve means for retarding the aromatics of the sample while the remainder of the sample passes through. The 13X MSCOT column separates the paraffins and naphthenes in the sample by carbon number. A first end of the 13X MSCOT column is connected to the valve means and the second end is connected to means for determining the amounts of paraffins and naphthenes separated by carbon number by the 13X MSCOT column. The mixed binary phase column separates the sample by components from $C_1$ through at least $C_8$. A first end of the mixed binary phase column is connected to the valve means and the second end is connected to means for determining the amounts of the sample separated by components from $C_1$ through at least $C_8$ by the fixed binary phase column. The nonpolar stationary phase column separates the aromatics in the sample. A first end of the nonpolar stationary phase column is connected to the valve means and a second end is connected to means for determining the amounts of aromatics separated by the nonpolar stationary phase column. A first and second means for supplying gas are connected to the valve means. The 13X MSCOT column and the nonpolar stationary phase column are provided with means for varying the temperature thereof. The valve means has at least a first and second position. In the first position the polar column is connected to the sample providing means, the 13X MSCOT column is connected to the polar column such that a portion of the effluent from the polar column passes through the 13X MSCOT column and the mixed binary phase column is connected to the polar column such that a portion of the effluent from the polar column passes through the mixed binary phase column. When the valve means is in the second position the flow through the polar column is reversed, the polar column is connected to the first end of the nonpolar stationary column such that the flow from the polar column enters the first end of the nonpolar stationary column, the first end of the 13X MSCOT column is connected to the second gas supply means and the first end of the mixed binary phase column is connected to the third gas supply means.

In addition, the present invention provides a method of analyzing a hydrocarbon sample comprising paraffins, naphthenes and aromatics. The hydrocarbon sample is injected into a first stream of carrier gas, and the first stream of carrier gas and the sample are passed through a polar column having a material for separating the aromatics from the remainder of the sample. The aromatics are retarded from the sample in the polar column, and the remainder of the sample and the first stream of carrier gas are allowed to pass through thereby providing a first effluent from the polar column which is split into at least first and second portions. The first effluent portion is passed through a 13X MSCOT column having a layer comprising a plurality of disunited particles of 13X material disposed on an inner surface of the column by filling the column with a suspension comprising a dispersive liquid and 13X material and flowing an inert gas through the column thereby leaving a layer comprising a plurality of disunited particles of the 13X material attached to the inner surface of the column for separating paraffins and naphthenes by carbon number. The second effluent portion is passed through a mixed binary phase column having a material for separating the sample by components from $C_1$ through at least $C_8$. The second effluent portion is separated by components from $C_1$ through at least $C_8$ in the mixed binary phase column. The flow of the first stream of carrier gas is reversed through the polar column to remove the aromatics from the polar column thereby providing a second effluent from the polar column. The second effluent portion is passed through a nonpolar stationary phase column having a material for separating the aromatics. The aromatics from the second effluent are separated in the nonpolar stationary phase column. A second stream of carrier gas is provided to the 13X MSCOT column, and a third stream of carrier gas is provided to the mixed binary phase column. The temperature of the 13X MSCOT column and the nonpolar stationary phase column are modified. The amounts of paraffins and naphthenes separated from the sample in the 13X MSCOT column, the amounts of components from $C_1$ through at least $C_8$ separated from the sample in the mixed binary phase column, and the amounts of aromatics separated from the sample in the nonpolar stationary phase column are detected.

The present invention provides a detailed analysis in approximately two hours of the paraffin, naphthene and aromatic breakdown of a hydrocarbon sample boiling below 255° C., including the $C_5/C_6$ ring naphthenes distribution. The data provided by the present invention can be used, for example, for inputting to a plant model to determine the steps that are necessary to optimize the reforming process. A plurality of columns and detectors are used concurrently to expand the analyzer's scope and to shorten the analysis time. In an alternative embodiment, the present invention can be provided with means for splitting the sample before it is passed through the polar column. A portion of the sample is provided to a column having a material for separating a predetermined inorganic component of the sample and means for detecting the amount of such component separated by the column.

Other objectives, advantages and applications of the present invention will be made apparent by the following detailed description of the preferred embodiments of the present invention.

BRIEF DESCRIPTION OF THE DRAWINGS

FIG. 2 is a chromatogram of the component by component separation of a typical hydrocarbon sample on the mixed binary phase column.

DETAILED DESCRIPTION OF THE PREFERRED EMBODIMENTS

Figure 1:
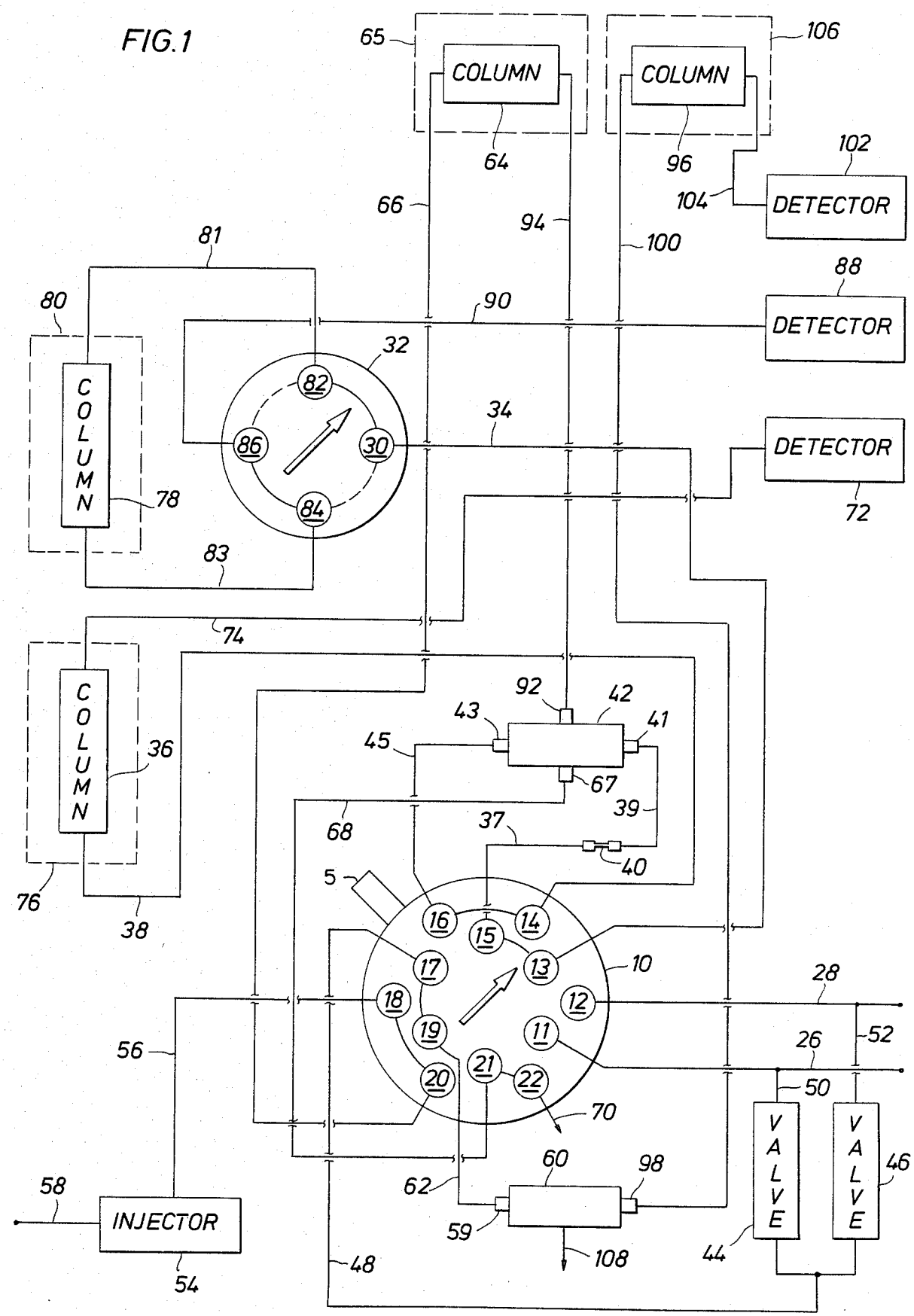
FIG. 1 is a diagrammatic view of a reformer process analyzer according to the present invention.
Figure 1A:
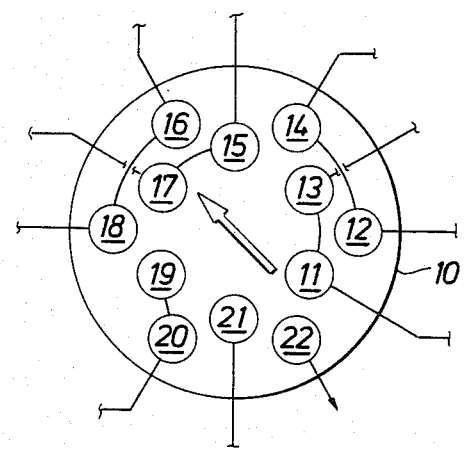
FIG. 1A is a diagrammatic view of a different position of a portion of the analyzer depicted in FIG. 1.

Referring to FIG. 1, one embodiment of the chromatographic analyzer of the present invention is illustrated. The analyzer has a valve 10 which has twelve ports labeled 11 through 22. Valve 10 has two positions in which the ports are connected internally in different configurations. When valve 10 is in the first position port 13 is connected to port 15, port 14 is connected to port 16, port 17 is connected to port 19, port 18 is connected to port 20, port 21 is connected to port 22, and ports 11 and 12 are not connected to any of the other ports. When valve 10 is switched to the second position as illustrated in FIG. 1A, port 11 is connected to port 13, port 12 is connected to port 14, port 15 is connected to port 17, port 16 is connected to port 18, port 19 is connected to port 20 and ports 21 and 22 are not connected to any of the other ports. Port 11 is connected to line 26 which is adapted to be connected to an inert gas supply such as helium. Port 12 is connected to line 28 which is adapted to be connected to an inert gas supply, such as helium. Port 13 is connected to port 30 of valve 32 by line 34. Port 14 is connected to one side of 13X MSCOT column 36 by line 38. Port 15 is connected by line 37 to flow restrictor 40. The other end of flow restrictor 40 is connected to port 41 of splitter 42 by line 39. Port 43 of splitter 42 is connected to port 16 of valve 10 by line 45. Port 17 is connected to the parallel combination of valves 44 and 46 by line 48. The other end of valve 44 is connected to line 26 by line 50, and the other end of valve 46 is connected to line 28 by line 52. Port 18 is connected to sample injector 54 by line 56. A line 58 which is adapted to be connected to an inert gas supply, such as helium or argon, is connected to injector 54 which can be either a manual or automatic injector. Preferably, injector 54 has a glass liner to minimize decomposition and adsorption of sensitive materials of the sample on the hot metal surface of the injector. Port 19 is connected to port 59 of splitter 60 by line 62. Port 20 is connected to one end of polar column 64 by line 66. Port 21 is connected to port 67 of splitter 42 by line 68. Port 22 is vented to atmosphere by line 70.

Column 36 is a 13X molecular sieve coated open tubular column. Finely ground 13X molecular sieve is combined with water to form a slurry which is pressured through a clean length of stainless steel capillary tubing. A purge is maintained to dry the column, thereby leaving the 13X sieve particles attached to the wall of the tubing. The finely divided particle layer provides a high resolution, type separation of naphthenes, iso-paraffins and paraffins boiling up to 255° C. Preferably, the tube consists of 15 meters of a stainless steel capillary tube with an inner diameter of 0.5 millimeters and contains approximately 1 mg. of 13X molecular sieve material having a particle size in the range of 0.4–12.0 microns. One end of column 36 is connected to port 14 of valve 10 by line 38, and the other end is connected to flame ionization detector 72 by line 74. Column 36 is positioned in temperature programmable oven 76 which is indicated by dotted lines. The temperature of oven 76 can be programmed by, for example, a suitable computer/controller, to provide suitable heating of column 36.

Column 78 is a mixed binary phase column for separating the sample by components from $C_1$ through at least $C_8$. Generally, the $C_9+$ materials are backflushed by valve 32. Preferably, column 78 is an n-hexadecane/-Fluorolube Oil LG-160 (FLO) capillary column having a film thickness of approximately 0.7 micrometers and is made of 30 meters of stainless steel capillary tubing having an inside diameter of 0.25 millimeters. The preferred concentration is 4.35 parts of n-hexadecane and 1 part FLO by volume; FLO is available from Fisher Scientific Co. Column 78 is positioned in isothermal oven 80 which is maintained at a temperature of, for example, 18.5° C. One end of column 78 is connected to port 82 of valve 32 by line 81, and the other end of column 78 is connected to port 84 of valve 32 by line 83. Port 86 of valve 32 is connected to flame ionization detector 88 by line 90. Valve 32 has two positions in which the ports are connected internally in different configurations. In the first position ports 30 and 82 are connected, and ports 84 and 86 are connected. In the second position, as indicated by the dotted lines, ports 30 and 84 are connected, and ports 82 and 86 are connected. Switching valve 32 from one position to the other reverses the flow through column 78.

Column 64 is a polar column for separating the aromatics from the remainder of the sample. Preferably, column 64 is a stainless steel tube having a length of 60 centimeters and an inside diameter of 2.3 millimeters, with BC-120 stationary phase, which is available from Supelco Inc. of Bellefonte, Pa., on Chromosorb-P AW Dimethylchlorosilane to make the saturates from aromatic separation. The mesh particle size is 100/120 M. One end of column 64 is connected to port 20 of valve 10 by line 66, and the other end of column 64 is connected to port 92 of splitter 42 by line 94. Column 64 is positioned in oven 65, which is indicated by dotted lines, and is maintained at a constant temperature. Column 96 is a nonpolar stationary phase column for separating the aromatics in the sample. Preferably, column 96 is a stainless steel support coated open tubular column having a length of 30 meters and an inside diameter of 0.5 millimeters which uses squalane for the separation. One end of column 96 is connected to port 98 of splitter 60 by line 100, and the other end of column 96 is connected to flame ionization detector 102 by line 104. Column 96 is located in a temperature programmable oven 106 which is indicated by dotted lines. The temperature of oven 106 is varied during the analysis. If desired, columns 64 and 96 can be located in the same oven. Splitter 60 has an additional port 108 which is vented to atmosphere; port 108 can include a flow restrictor to limit the flow to atmosphere. Flame ionization detectors 72, 88 and 102 can include chart recorders and/or electronic circuitry to provide a signal suitable for inputting to a computer/controller. The operation of the analyzer, including the operation of the valves, the temperature programming of the ovens, and the output recording from the detectors, can be under the control of a master computer/controller 5. This master computer/controller 5 can also include functions for data manipulation and output formatting, such as the calculation of the paraffins, naphthenes and aromatics and the $C_5/C_6$ ring naphthenes distribution as is known in the art.

The operation of the reformer process analyzer of the present invention can be described as follows. The sample is injected into the analyzer by injector 54. The carrier gas flow from line 58 carries the sample from injector 54 through line 56 to port 18 of valve 10. The sample then passes from port 18 to port 20 from which it passes through line 66 to column 64. Column 64 retards the aromatics of the sample and allows the remainder of the sample and carrier gas to pass through to line 94. Line 94 provides the remainder of the sample to port 92 of splitter 42. Splitter 42 splits the remainder of the sample three ways such that one portion passes through port 43 of splitter 42, through line 45 to port 16 of valve 10 to port 14 from which it passes through line 38 to column 36. A second portion of the sample passes through port 67 of splitter 42 to line 68 which is connected to port 21 of valve 10. The sample passes from port 21 to port 22 from which it is exhausted to atmosphere by line 70. The third portion of the sample passes through port 41 of splitter 42, line 39, and restrictor 40 to line 37. The sample passes through line 37 to port 15 of valve 10 and is exhausted therefrom by port 13 to line 34. The sample passes through line 34 to port 30 of valve 32 and is exhausted therefrom at port 82 into line 81 and hence column 78. The sample passes through column 78, and the effluent from column 78 passes through line 83 to valve 30 at port 84 and is exhausted therefrom at port 86 into line 90 to flame ionization detector 88. Carrier gas from lines 26 and 28 flows into line 50 and valve 44 and line 52 and valve 46, respectively. The combined flow then passes through line 48 to port 17 and is exhausted from valve 10 at port 19. Line 62 provides the carrier gas to port 59 of splitter 60. A portion of the carrier gas is exhausted to atmosphere by line 108 and the remainder passes through port 98 of splitter 60 to line 100. From line 100 the carrier gas passes through column 96, thus purging it, and passes through line 104 to flame ionization detector 102. Before valve 10 is switched from its first position valves 44 and 46 are closed in a predetermined time sequence to raise the carrier gas pressure slightly, 2-5 psi, above normal operating pressures in lines 26 and 28 after valve 10 is switched to its second position. This increased pressure prevents diffusing of the sample from columns 36 and 78 into lines 38 and 81, respectively. For optimum separation two different molecular weight carrier gases should be used, such as argon in line 58 and heluim in lines 26 and 28.

Before benzene would elute from column 64, valve 10 is switched from its first position to its second position which is indicated in FIG. 1A. Carrier gas is supplied by line 26 to port 11 of valve 10 and exhausted from valve 10 at port 13 into line 34. From line 34 the carrier gas passes through port 30 of valve 32 and is exhausted therefrom at port 82 into line 81 and then column 78. The carrier gas flows through column 78 into port 84 of valve 32 and is exhausted therefrom at port 86 into line 90 from which it is provided to flame ionization detector 88. Column 78 separates the sample by components from $C_1$ through at least $C_8$ as detected by flame ionization detector 88. The component separation of the sample as detected by flame ionization detector 88 is indicated in FIG. 2. The peaks identified in FIG. 2 are defined in Table 1.

TABLE 1

Identification of Chromatogram (FIG. 2)

| Peak Number | Compound |
|---|---|
| 1 | Butanes and Lighter |
| 2 | Isopentane |
| 3 | n-Pentane |
| 4 | 2,2-Dimethylbutane |
| 5 | Cyclopentane |
| 6 | 2,3-Dimethylbutane |
| 7 | 2-Methylpentane |
| 8 | 3-Methylpentane |
| 9 | n-Hexane |
| 10 | Methylcylopentane |
| 11 | 2,2-Dimethylpentane |
| 12 | 2,4-Dimethylpentane |
| 13 | 2,2,3-Trimethylbutane |
| 14 | Benzene |
| 15 | Cyclohexane |
| 16 | 3,3-Dimethylpentane |
| 17 | 1,1-Dimethylcylopentane |
| 18 | 2-Methylhexane + 2,3-dimethylpentane |
| 19 | 1,cis-3-Dimethylcyclopentane |
| 20 | 3-Methylhexane |
| 21 | 1,trans-3-Dimethylcyclopentane |
| 22 | 1,trans-2-Dimethylcyclopentane |
| 23 | 3-Ethylpentane |
| 24 | 2,2,4-Trimethylpentane |
| 25 | n-Heptane |
| 26 | 1,cis-2-Dimethylcyclopentane |
| 27 | Methylcyclohexane |
| 28 | 1,1,3-Trimethylcyclopentane |
| 29 | 2,2-Dimethylhexane |
| 30 | Ethylcyclopentane |
| 31 | 2,5-Dimethylhexane |
| 32 | 2,4-Dimethylhexane + 2,2,3-trimethylpentane |
| 33 | 1,trans-2,cis-4-Trimethylcyclopentane |
| 34 | 1,trans-2,cis-3-Trimethylcyclopentane |
| 35 | 2,3,4-Trimethylpentane |
| 36 | 1,1,2-Trimethylcyclopentane |
| 37 | 2-Methyl-3-ethylpentane |
| 38 | 2,3-Dimethylhexane |
| 39 | 1,cis-2,trans-4-Trimethylcyclopentane |
| 40 | 1,cis-2,trans-3-Trimethylcyclopentane |
| 41 | 1,cis-2,cis-4-Trimethylcyclopentane + 2-methylheptane + 3-methyl-3-ethylpentane + 3,4-dimethylhexane |
| 42 | 4-methylheptane |
| 43 | 3-Ethylhexane |
| 44 | 3-Methylheptane + 1,1-dimethylcyclohexane |
| 45 | 1,trans-4-Dimethylcyclohexane + 1,cis-3-dimethylcyclohexane |
| 46 | 1-Methyl-cis-3-ethylcyclopentane |
| 47 | 1-Methyl-trans-3-ethylcyclopentane + 1-methyl-trans-2-ethylcyclopentane + 1-methyl-1-ethylcyclopentane |
| 48 | 1,cis-2,cis-3-Trimethylcyclopentane + 1,trans- |

TABLE 1-continued
Identification of Chromatogram (FIG. 2)

| Peak Number | Compound |
|---|---|
|  | 2-dimethylcyclohexane |
| 49 | 1,trans-3-Dimethylcyclohexane + 1,cis-4-dimethylcyclohexane |
| 50 | C$_8$ Paraffin |
| 51 | Isopropylcyclopentane |
| 52 | n-Octane |
| 53 | C$_8$ Paraffin |
| 54 | 1-Methyl-cis-2-ethylcyclopentane |
| 55 | C$_8$ Paraffin |
| 56 | 1,cis-2-Dimethylcyclohexane |
| 57 | C$_8$ Paraffin |
| 58 | Ethylcyclohexane |
| 59 | n-Propylcyclopentane |
| 60 | C$_8$ Paraffin |
| 61 | C$_8$ Paraffin |
| 62 | C$_{9+}$ Saturates |

Figure 4:
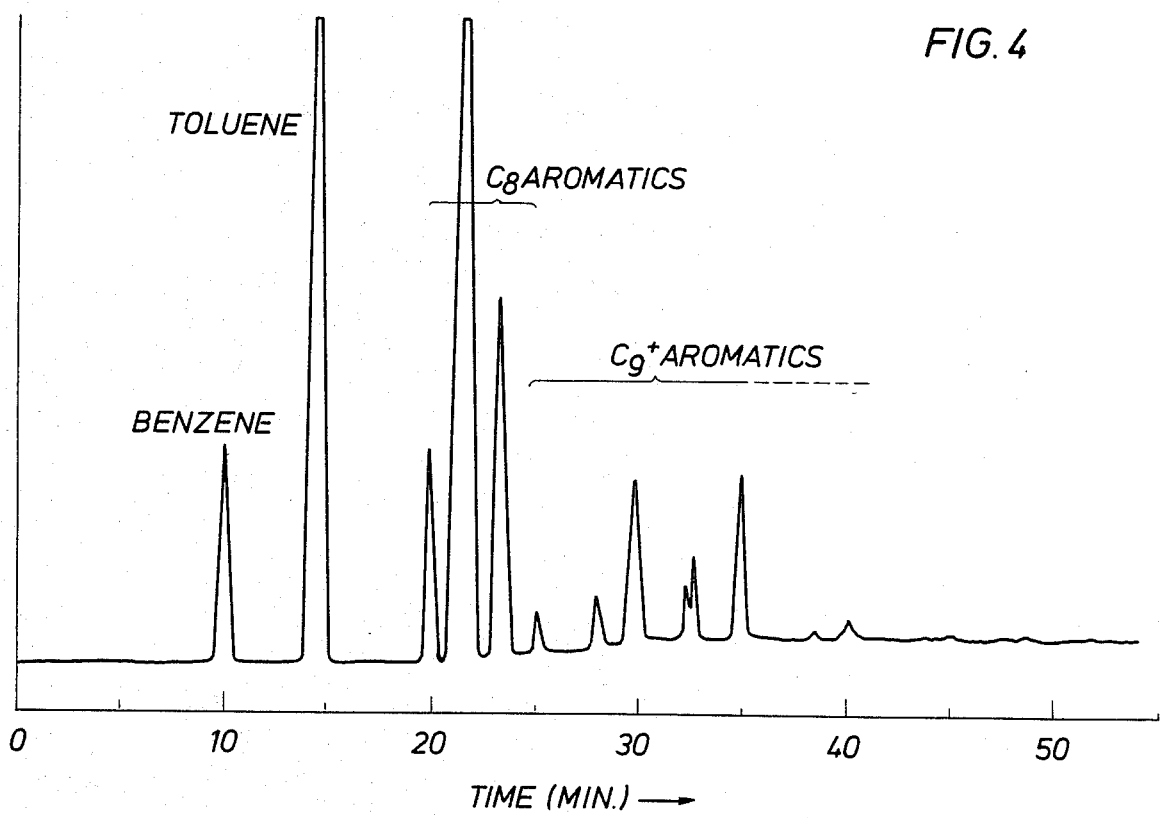
FIG. 4 is a chromatogram showing the separation of the aromatics from a typical hydrocarbon sample on the nonpolar stationary phase column.
Figure 3:
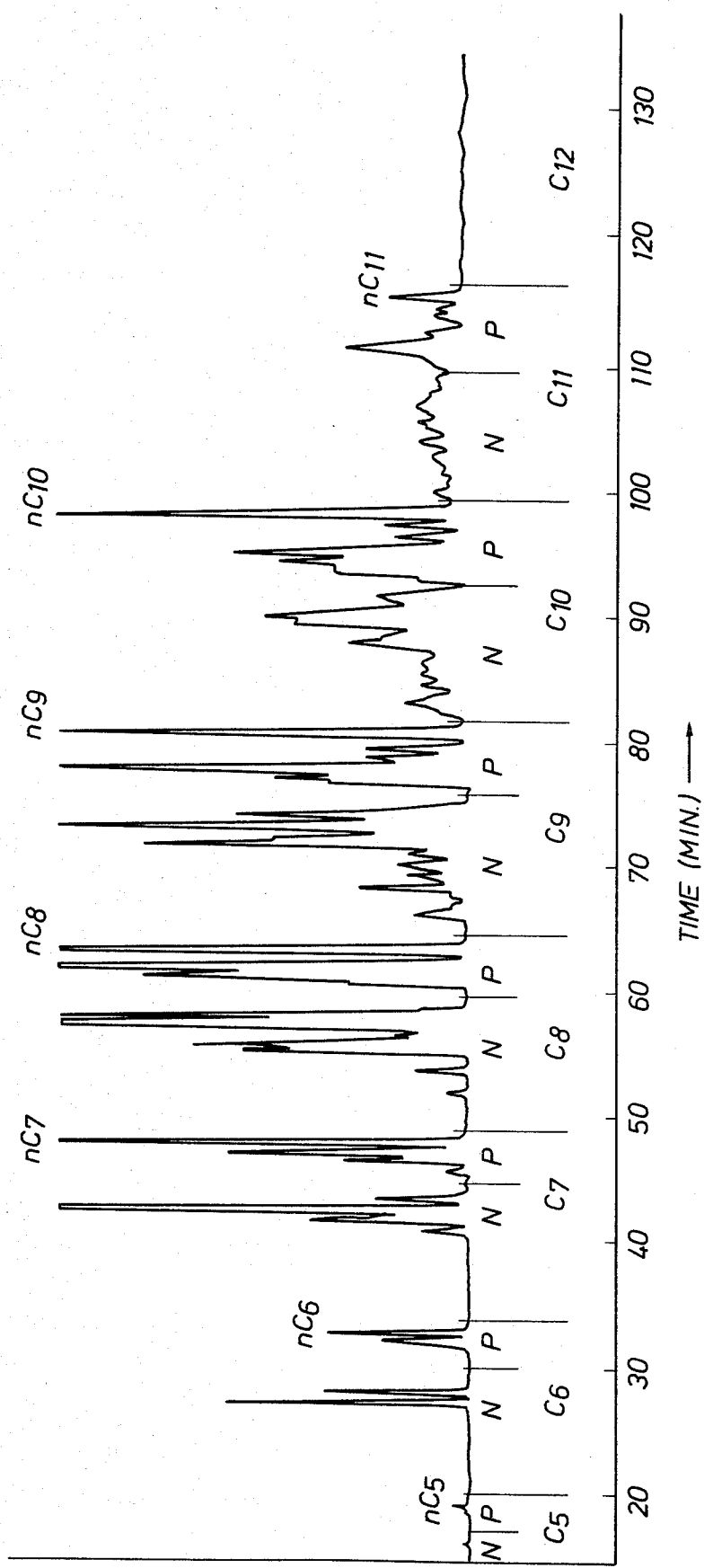
FIG. 3 is a chromatogram of the paraffin-naphthene separation of a typical hydrocarbon sample on the 13X MSCOT column.

Carrier gas flows from line 28 into port 12 of valve 10 and is exhausted therefrom at port 14 into line 38 which provides it to one end of column 36. The carrier gas passes through column 36 and is exhausted therefrom to line 74 from which it is provided to flame ionization detector 72. At the point at which valve 10 is switched from the first position to its second position oven 76 begins its temperature program. Column 36 separates the paraffins and naphthenes in the sample by carbon number as detected by flame ionization detector 72. FIG. 3 is a typical chromatogram of the separation provided by column 36. Carrier gas continues to flow through line 58, injector 54, line 56 and port 18 of valve 10. The gas is exhausted from port 16 of valve 10 into line 45 from which it enters port 43 of splitter 42. The carrier gas then flows through port 92 of splitter 42 into line 94 to column 64. It should be noted that this flow is in the opposite direction of the flow through column 64 when valve 10 is in its first position; this reversed flow backflushes the aromatics that were retarded by column 64 during the time that the sample was injected when valve 10 was in its first position. The flow backflushes the aromatics from column 64 into line 66 to port 20 of valve 10 and is exhausted therefrom at port 19 into line 62. Line 62 provides the flow to port 59 of splitter 60 which then splits a portion of this flow to atmosphere by way of line 108 and passes the remainder through port 98 into line 100. Line 100 provides the flow to column 96 which separates the aromatics as detected by flame ionization detector 102 which is connected to column 96 by line 104. When valve 10 is switched from its first position to its second position oven 106 is progressed through its temperature program. The sample chromatogram obtained with column 96 is provided in FIG. 4. At a predetermined time valve 32 is switched from its first position to its second position so that the flow through column 78 is reversed to backflush column 78.

Figure 5:
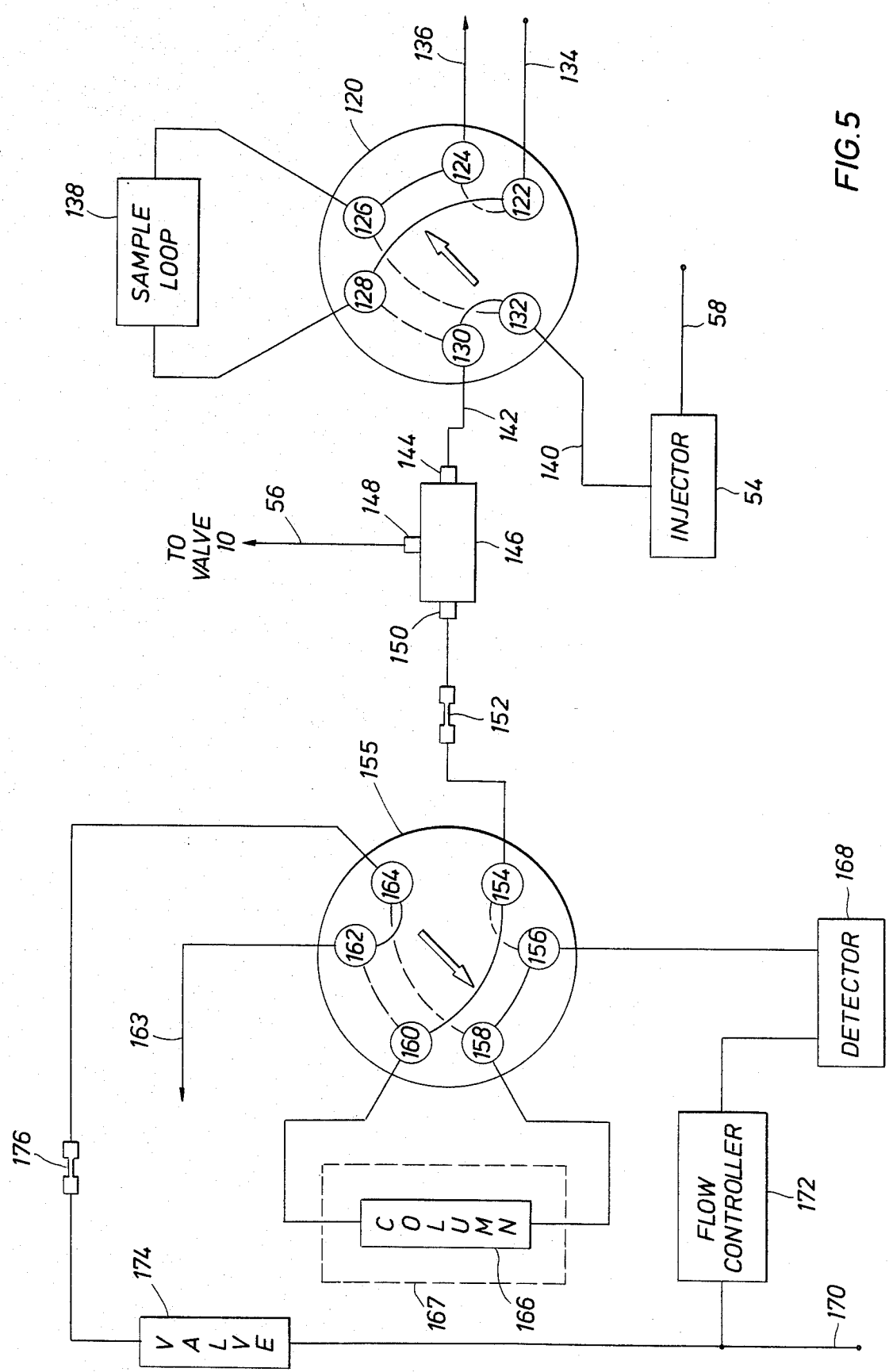
FIG. 5 is an alternative embodiment of the present invention.

Referring to FIG. 5, an alternative embodiment of the present invention is provided in which an additional branch for detecting an inorganic component of the sample is incorporated with the paraffin, naphthene and aromatic analysis scheme described in reference to FIG. 1. A 6-port valve 120 has ports 122, 124, 126, 128, 130 and 132. When valve 120 is in its first position port 122 is connected to port 128, port 124 is connected to port 126 and port 130 is connected to port 132. When valve 120 is in its second position port 122 is connected to port 124, port 126 is connected to port 132 and port 128 is connected to port 130. Port 122 is connected to a line 134 which is adapted for providing a gas sample to the analyzer system. Port 124 is connected to a line 136 which is vented to atmosphere. A variable sample loop 138 is connected across ports 126 and 128. Port 132 is connected to injector 54 by line 140. Injector 54 is the same injector as described hereinabove in reference to FIG. 1, and again it is provided with a carrier gas, such as helium or argon by line 58. Port 130 is connected by line 142 to port 144 of splitter 146. Port 148 of splitter 146 is connected to line 56 which carries a portion of the sample to port 18 of valve 10 for analysis as described hereinabove in reference to FIG. 1. The other portion of the sample passes through port 150 of splitter 146 through flow resistor 152 into port 154 of valve 155. Valve 155 is a 6-port valve having ports 154, 156, 158, 160, 162 and 164. When valve 155 is in its first position port 154 is connected to port 160, port 156 is connected to port 158 and port 162 is connected to port 164. When valve 155 is in its second position port 154 is connected to part 156, port 160 is connected to port 162 and port 158 is connected to port 164. Port 156 is connected to detector 168 which can be, for example, a thermal conductivity detector for detecting a particular inorganic component of the sample. Column 166 which can be located in oven 167 is connected across ports 158 and 160. Port 162 is connected to line 163 which is vented to atmosphere. Port 164 is connected to valve 174 through flow restrictor 176. Line 170 which is adapted to be connected to a gas supply means, such as argon, provides gas to both valve 174 and flow controller 172. Flow controller 172 provides a reference gas to detector 168. In this embodiment valve 120 allows the selection of either a liquid sample injected by injector 54 or a gas sample provided by line 134. Flow restrictor 152 is sized to provide the appropriate flow to column 166. Valve 155 allows the flow through column 166 to be reversed to backflush column 166, thereby shortening the analysis time. Flow restrictor 176 modifies the flow to the proper amount for column 166 during backflushing. Valve 174 is interlocked with valve 155 so that valve 174 is closed when valve 155 is in its first position and, valve 174 is open when valve 155 is in its second position. If desired valve 174 and flow restrictor 176 can be omitted and valve 155 can be replaced by a four port valve.

It is to be understood that variations and modifications of the present invention can be made without departing from the scope of the invention. It is also to be understood that the scope of the invention is not to be interpreted as limited to the specific embodiments disclosed herein, but only in accordance with the appended claims when read in light of the foregoing disclosure.

We claim as our invention:

1. A method for analyzing a hydrocarbon sample for paraffins, naphthenes and aromatics, comprising:
   separating said aromatics of said sample from said paraffins and naphthenes of said sample;
   separating and detecting said paraffins and naphthenes by carbon number;
   separating and detecting individual saturated components of said sample; and
   separating and detecting individual components of said aromatics.

2. A method as described in claim 1, wherein said separating and detecting of said individual saturated components is for components having a number of carbon atoms substantially in the range from one carbon atom to eight carbon atoms.

3. A method as described in claim 2, wherein said separating of said aromatics from said naphthenes and paraffins is conducted with a gas chromatograph column and is stopped in functional relationship to the elution of benzene from said column.

4. A method as described in claim 1, further comprising:
   initially dividing said sample into a first and second portion;
   separating and detecting a predetermined inorganic component in said first portion of said sample; and
   wherein said separating of said aromatics from said naphthenes and paraffins is conducted with said second portion of said sample.

5. Apparatus for analyzing a hydrocarbon sample, comprising:
   means for separating aromatics of said sample from paraffins and naphthenes of said sample;
   means for separating and detecting said naphthenes and paraffins by carbon number;
   means for separating and detecting individual saturated components of said sample; and
   means for separating and detecting individual components of said aromatics.

6. An apparatus as described in claim 5, further comprising means for separating and detecting a preselected inorganic component.

7. An apparatus as described in claim 5, wherein said means for separating aromatics from paraffins and naphthenes comprises a polar column.

8. An apparatus as described in claim 7, wherein said means for separating and detecting paraffins and naphthenes comprises a 13X molecular sieve coated open column.

9. An apparatus as described in claim 8, wherein said means for separating and detecting individual saturated components comprises a mixed binary phase column.

10. An apparatus as described in claim 9, wherein said means for separating and detecting individual components of said aromatics comprises a non-polar stationary phase column.

11. An apparatus as described in claim 10, further comprising means for controlling the temperature of said 13X molecular sieve column.

12. An apparatus as described in claim 11, further comprising means for controlling the temperature of said non-polar column.

13. An apparatus as described in claim 5, further comprising controller means for controlling and operating said means for separating aromatics from paraffins and naphthenes, said means for separating and detecting paraffins and naphthenes, said means for separating and detecting individual saturated components and said means for separating and detecting individual components of said aromatics.

14. An apparatus for analyzing a hydrocarbon sample comprising paraffins, naphthenes and aromatics, said apparatus comprising:
   means for providing a sample;
   a first means for supplying gas connected to said sample providing means;
   a first valve means connected to said sample providing means and having at least a first and second position;
   a polar column connected to said first valve means for retarding the aromatics of said sample while the remainder of said sample passes through;
   a 13X MSCOT column for separating paraffins and naphthenes in said sample by carbon number having a first and connected to said first valve means and a second end connected to means for determining the amounts of paraffins and naphthenes separated by carbon number by said 13X MSCOT column;
   means for varying the temperature of said 13X MSCOT column;
   a mixed binary phase column for separating said sample by individual saturated components having a number of carbon atoms from one through at least eight, having a first end connected to said first valve means and a second end connected to means for determining the amounts of said sample separated by components having a number of carbon atoms from one through at least eight by said mixed binary phase column;
   means for maintaining said mixed binary phase column at a predetermined temperature;
   a non-polar stationary phase column for separating the individual aromatics components in said sample, having a first end connected to said first valve means and a second end connected to means for determining the amounts of individual components of said aromatics separated by said non-polar stationary phase column;
   means for varying the temperature of said non-polar stationary phase column;
   a second means for supplying gas connected to said first valve means;
   a third means for supplying gas connected to said first valve means; and
   wherein said first valve means in said first position, interconnects said polar column to said injecting means, and interconnects said 13X MSCOT column and said mixed binary column to said polar column such that a portion of the effluent from said polar column passes through said 13X MSCOT column and said mixed binary phase column and in said second position reverses flow through said polar column and interconnects said polar column to said first end of said non-polar stationary column such that the flow from said polar column enters said first end of said non-polar stationary column, interconnects said first end of said 13X MSCOT column to said second gas supply means, and interconnects said first end of said mixed binary phase column to said third gas supply means.

15. An apparatus as described in claim 14, wherein said apparatus further comprises a second valve means connected to said first valve means and said mixed binary phase column, said second valve means having first and second positions such that in said first position said first end of said mixed binary phase column is connected to said first valve means and said second end is connected to said means for determining the amounts of saturated components of said sample separated by components having a number of carbon atoms from one through at least eight by said mixed binary phase column and such that in said second position said second end of said mixed binary phase column is connected to said first valve means and said first end of said mixed binary phase column is connected to said means for determining the amounts of said sample separated by components having a number of carbon atoms from one through at least eight by said mixed binary phase column.

16. An apparatus as described in claim 14, wherein said apparatus further comprises means to switch said first valve means from said first position to said second position at a time functionally related to the elution time of benzene.

17. An apparatus as described in claim 14, wherein said apparatus further comprises means connected to said sample providing means for separating a portion of the sample, a first column connected to said separating means for separating a predetermined inorganic component from said sample and means for determining the amount of said predetermined inorganic component separated from said sample by said first column.

18. An apparatus as described in claim 17, wherein said sample providing means is adapted to provide a liquid sample and wherein said apparatus further comprises means adapted for providing a gas sample and a third valve means connected to said splitting means and said liquid sample providing means, said third valve means having at least a first and second position such that in said first position said liquid sample providing means is connected to said splitting means and said means for providing a gas sample is not connected to said splitting means and such that in said second position said means for providing a gas sample is connected to said splitting means and said means for providing a liquid sample is not connected to said splitting means.

19. An apparatus as described in claim 17, wherein said apparatus further comprises a fourth valve means connected to said first column, said first valve means having a first position in which flow is directed through said first column in a first direction and a second position in which flow is directed through said first column in the opposite direction.

20. A method of analyzing a hydrocarbon sample comprising paraffins, naphthenes and aromatics, said method comprising the steps of:
injecting said hydrocarbon sample into a first stream of carrier gas;
passing said first stream of carrier gas and sample through a polar column having a material for retarding aromatics from the remainder of said sample;
retarding in said polar column the aromatics from said sample and allowing the remainder of said sample and said first stream of carrier gas to pass through thereby providing a first effluent from said polar column;
splitting said first effluent from said polar column into at least first and second portions;
passing said first portion through a 13X MSCOT column for separating paraffins and naphthenes by carbon number;
passing said second portion through a mixed binary phase column having a material for separating said second portion by individual saturated components having a number of carbon atoms from one through at least eight;
separating in said mixed binary phase column the individual saturated components having a number of carbon atoms from one through at least eight in said second portion;
reversing the flow of said first stream of carrier gas through said polar column to remove said aromatics from said polar column thereby providing a second effluent from said polar column;
passing the second effluent through a nonpolar stationary phase column having a material for separating the individual components of the aromatics;
separating in said nonpolar stationary phase column said aromatics in said second effluent;
providing a second stream of carrier gas to said 13X MSCOT column;
providing a third stream of carrier gas to said mixed binary phase column;
modifying the temperature of said 13X MSCOT column;
modifying the temperature of said nonpolar stationary phase column;
detecting the amounts of paraffins and naphthenes separated by carbon number from said sample in said 13X MSCOT column;
detecting the amounts of individual saturated components having a number of carbon atoms from one through at least eight separated in said mixed binary phase column; and
detecting the amounts of individual aromatics separated in said nonpolar stationary phase column.

21. A method as described in claim 20, wherein said step of reversing the flow of said first stream of carrier gas through said polar column is performed at a time functionally related to the elution time of benzene.

22. A method as described in claim 20, further comprising the step of reversing the flow through said mixed binary phase column at a time functionally related to the elution time of individual components having a number of carbon atoms from one through at least eight.

23. A method as described in claim 20, further comprising the steps of: splitting said sample before passing it through said polar column; passing a portion of said split sample through a first column containing a material for separating a predetermined inorganic component from said split sample; separating said predetermined inorganic component in said first column; and detecting the amount of said predetermined inorganic component separated from said portion of said split sample in said first column.

24. A method as described in claim 23, further comprising the step of reversing the flow through said first column at a predetermined time.

25. A method as described in claim 20, further comprising the step of flowing a gas through said nonpolar stationary phase column until a time functionally related to the elution time of benzene in said polar column.

26. Apparatus for analyzing a hydrocarbon sample, comprising:
a 13X molecular sieve coated open column for separating paraffins and naphthenes by carbon number;
a mixed binary phase column for separating individual saturated components;
a nonpolar stationary phase column for separating individual aromatics;
a polar column for separating naphthenes and paraffins from aromatics selectively interconnectable with said 13X molecular sieve column and mixed binary phase column, and with said nonpolar column.

27. The apparatus described in claim 26, further comprising means for controlling the temperature of said 13X molecular sieve column.

28. The apparatus described in claim 27, further comprising means for controlling the temperature of said nonpolar column.

29. The apparatus described in claim 26, further comprising a first column for separating at least one preselected inorganic component from said sample operatively interconnected with said polar column.

30. The apparatus described in claim 26, wherein said polar column is selectively interconnected with said nonpolar column in functional relationship to the elution time of benzene from said polar column.

* * * * *